(12) United States Patent
Tokubuchi et al.

(10) Patent No.: US 9,433,212 B2
(45) Date of Patent: Sep. 6, 2016

(54) PLANT GROWTH REGULATOR AND METHOD FOR USING THE SAME

(75) Inventors: Nao Tokubuchi, Tokyo (JP); Shingo Tamura, Tokyo (JP); Takao Aoki, Osaka (JP); Ken Kuriyama, Tokyo (JP)

(73) Assignee: NIHON NOHYAKU CO., LTD., Tokyo (JP)

(*) Notice: Subject to any disclaimer, the term of this patent is extended or adjusted under 35 U.S.C. 154(b) by 192 days.

(21) Appl. No.: 14/123,370

(22) PCT Filed: Jun. 5, 2012

(86) PCT No.: PCT/JP2012/064414
§ 371 (c)(1),
(2), (4) Date: Feb. 12, 2014

(87) PCT Pub. No.: WO2012/169473
PCT Pub. Date: Dec. 13, 2012

(65) Prior Publication Data
US 2014/0213656 A1    Jul. 31, 2014

(30) Foreign Application Priority Data
Jun. 6, 2011 (JP) .................................. 2011-126766

(51) Int. Cl.
*A61K 31/16* (2006.01)
*A01N 37/18* (2006.01)
*A01N 41/10* (2006.01)
*A01G 7/06* (2006.01)

(52) U.S. Cl.
CPC .............. *A01N 41/10* (2013.01); *A01G 7/06* (2013.01)

(58) Field of Classification Search
CPC ............................ A01N 41/10; A01N 25/04
USPC .................................................. 514/616, 154
See application file for complete search history.

(56) References Cited

U.S. PATENT DOCUMENTS

| | | | |
|---|---|---|---|
| 5,039,693 | A | 8/1991 | Okada et al. |
| 6,603,044 | B1 | 8/2003 | Tohnishi et al. |
| 2004/0077500 | A1 | 4/2004 | Sakata et al. |
| 2006/0063724 | A1 | 3/2006 | Konze et al. |
| 2007/0142463 | A1 | 6/2007 | Fischer et al. |
| 2007/0265266 | A1 | 11/2007 | Fischer et al. |
| 2008/0051457 | A1 | 2/2008 | Nakao et al. |
| 2008/0145349 | A1 | 6/2008 | Sakata et al. |
| 2010/0087542 | A1* | 4/2010 | Reckmann ........... A01N 37/30 514/616 |
| 2011/0152077 | A1* | 6/2011 | Ilg ....................... A01N 43/82 504/100 |
| 2012/0094834 | A1* | 4/2012 | Frank ................... A01N 43/653 504/117 |
| 2014/0148493 | A1* | 5/2014 | Tamura ................. A01N 43/56 514/406 |
| 2014/0256687 | A1* | 9/2014 | Tamura ................. A01N 57/14 514/136 |

FOREIGN PATENT DOCUMENTS

| | | |
|---|---|---|
| CN | 101755750 A | 6/2010 |
| CN | 102047907 A | 5/2011 |
| CN | 102302009 A | 1/2012 |
| CN | 102630677 A | 8/2012 |
| CN | 103039457 A | 4/2013 |
| CN | 103636611 A | 3/2014 |
| EP | 1380209 A1 | 1/2004 |
| JP | 381266 A | 4/1991 |
| JP | 2001131141 A | 5/2001 |
| JP | 200312415 A | 1/2003 |
| JP | 2006131516 A | 5/2006 |
| WO | WO-02087334 A1 | 11/2002 |
| WO | WO-2004034786 A1 | 4/2004 |
| WO | WO-2005004603 A1 | 1/2005 |
| WO | WO-2005004604 A1 | 1/2005 |
| WO | WO-2006022225 A1 | 3/2006 |

OTHER PUBLICATIONS

International Preliminary Report on Patentability in PCT/JP2012/064414 dated Dec. 10, 2013. (English Translation).
International Search Report in corresponding PCT/JP2012/064414 dated Aug. 7, 2012.
Written Opinion in corresponding PCT/JP2012/064414 dated Aug. 7, 2012.
"Novel Broad-Spectrum, Safe Ryanodine Receptor Insecticide", Chinese Journal of Pesticides, vol. 44, No. 11, Nov. 2005. (English Translation).
Y. Cao et al., The Synthesis and Insecticidal Activity of Flubendiamide, Modern Agrochemicals, vol. 5, No. 3 (2006).
Extended European Search Report in corresponding PCT/JP2012/066473 dated Jan. 5, 2015.
International Preliminary Report in PCT/JP2012/066473 dated Jan. 7, 2014 (English Translation).
Written Opinion in corresponding PCT/JP2012/066473 dated Aug. 10, 2012.
International Search Report in corresponding PCT/JP2012/066473 dated Aug. 10, 2012.

* cited by examiner

*Primary Examiner* — My-Chau T Tran
(74) *Attorney, Agent, or Firm* — Marshall, Gerstein & Borun LLP

(57) ABSTRACT

Provided is a novel plant growth regulator. The disclosed plant growth regulator comprises flubendiamide as an active ingredient.

2 Claims, No Drawings

PLANT GROWTH REGULATOR AND METHOD FOR USING THE SAME

TECHNICAL FIELD

The present invention relates to a plant growth regulator comprising flubendiamide as an active ingredient, and a method for using the same.

BACKGROUND ART

Flubendiamide is an insecticidal compound and commercially available as an agricultural and horticultural insecticide (see Patent Literature 1 and Non Patent Literature 1, for example). However, these prior art references or the like neither describe nor suggest any plant growth regulating effect of flubendiamide.

CITATION LIST

Patent Literature

Patent Literature 1: JP-A 2001-131141

Non Patent Literature

Non Patent Literature 1:
The Pesticide Manual 14th Edition (British Crop Production Council)

SUMMARY OF INVENTION

Technical Problem

In recent years, agrochemicals having growth promoting effect on crops, etc. (plant growth regulators) have been tried out with the aim of sound growth and yield increase of crops. However, conventional plant growth regulators are disadvantageous in that the plant growth regulating effect is insufficient in some kinds of crops, some growing conditions, etc. and therefore novel plant growth regulators are still desired.

Solution to Problem

In order to develop novel plant growth regulators, the present inventors have investigated the effect of various compounds on plant growth regulation. As a result, the present inventors have found that a known agricultural and horticultural insecticide flubendiamide has an excellent plant growth regulating effect and completed the present invention.

That is, the present invention relates to the following.
[1] A plant growth regulator comprising flubendiamide as an active ingredient.
[2] A method for using a plant growth regulator, comprising treatment of target crops or soil in the vicinity of the target crops with the plant growth regulator according to the above [1].
[3] The method according to the above [2], wherein the treatment is spray treatment of the target crops, or spray treatment or drench treatment of the soil in the vicinity of the target crops.
[4] A method for increasing the yield of target crops, comprising treatment of target crops or soil in the vicinity of the target crops with the plant growth regulator according to the above [1].
[5] A method for promoting the growth of target crops, comprising treatment of target crops or soil in the vicinity of the target crops with the plant growth regulator according to the above [1].

Advantageous Effects of Invention

According to the present invention, the plant growth regulator and the method for using the same can promote sound growth of crops and produce excellent plant growth regulating effects on the crops, including rooting promotion; earlier initiation of rooting; increase of the numbers of leaves, stems, panicles and unhulled rice grains; promotion of tillering; plant height growth; stem enlargement; growth promotion; increase of resistance to drought, salts, low temperatures and high temperatures; reduction of lower leaf senescence; and coloring and ripening acceleration, sugar content increase, quality improvement, yield increase, etc. of harvestable plant parts of fruits, cereals, potatoes, legumes, etc. Further, the plant growth regulator and the method for using the same can utilize the previously known effect of flubendiamide as an agricultural and horticultural insecticide, and thus are also remarkably effective for control of insect pests such as Lepidopteran insect pests.

DESCRIPTION OF EMBODIMENTS

Flubendiamide (general name; chemical name: 3-iodo-N'-(2-mesyl-1,1-dimethylethyl)-N-{4-[1,2,2,2-tetrafluoro-1-(trifluoromethyl)ethyl]-o-tolyl}phthalamide), which is the active ingredient of the plant growth regulator of the present invention, can be produced according to the production method disclosed by Patent Literature 1, and is commercially available from NIHON NOHYAKU CO., LTD. under the trade name of "Phoenix WDG (water-dispersible granule)."

As the active ingredient flubendiamide of the plant growth regulator of the present invention, commercial flubendiamide formulations may be used as they are. Alternatively, flubendiamide may be produced according to the production method disclosed by Patent Literature 1 and then prepared into a formulation. For the preparation of a formulation, the active ingredient and an appropriate inactive carrier, and if needed an adjuvant are blended in an appropriate ratio, and through the step of dissolution, separation, suspension, mixing, impregnation, adsorption and/or adhesion, are formulated into an appropriate form for application, such as a flowable, an emulsifiable concentrate, a soluble concentrate, a wettable powder, a water-dispersible granule, a granule, a dust, a tablet and a pack.

The inactive carrier may be a solid or liquid carrier. Examples of the solid carrier include natural minerals, such as quartz, clay, kaolinite (kaolin), pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). These solid carriers may be used alone or in a combination of two or more kinds.

Examples of the liquid carrier include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as gamma-butyrolactone; amides, such as dimethylformamide, diethylformamide, dimethylacetamide and N-alkyl pyrrolidone (N-methylpyrrolidone etc.); nitriles, such as acetonitrile; sulfur compounds, such as dimethyl sulfoxide; vegetable oils, such as soybean oil, rapeseed oil, cotton seed oil and castor oil; and water. These liquid carriers may be used alone or in a combination of two or more kinds.

Examples of the adjuvant include surfactants used as a dispersant, a wetting agent, a spreader, a sticking/spreading agent, etc., binders, tackifiers, thickeners, colorants, antifreezing agents, anti-caking agents, disintegrants and stabilizing agents. If needed, preservatives, plant fragments, etc. may be additionally used. These adjuvants may be used alone or in a combination of two or more kinds.

Examples of the surfactants used as a dispersant, a wetting agent, a spreader, a sticking/spreading agent, etc. include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. These surfactants may be used alone or in a combination of two or more kinds.

Examples of the binders or the tackifiers include carboxymethyl cellulose and salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch derivatives and polysaccharides; and inorganic fine powders, such as high grade bentonite and fumed silica (white carbon).

Examples of the colorants include inorganic pigments, such as iron oxide, titanium oxide and prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds. Examples of the preservatives include potassium sorbate and 1,2-benzothiazolin-3-one.

Further, other adjuvants including functional spreading agents, activity enhancers such as metabolic inhibitors (piperonyl butoxide etc.), antioxidants (BHT etc.) and ultraviolet absorbers can also be used if needed.

The flubendiamide content of the plant growth regulator of the present invention can be adjusted as needed and is not particularly limited, but is usually about 0.01 to 90% by mass. For example, in the case where the plant growth regulator is a dust or a granule, the flubendiamide content is preferably about 0.1 to 50% by mass, and in the case where the plant growth regulator is an emulsifiable concentrate, a wettable powder, a flowable, a water-dispersible granule or the like, the flubendiamide content is preferably about 0.1 to 90% by mass.

In the plant growth regulator of the present invention and the method for using the same, target crops may be any kinds of useful crops, and the examples include, but are not limited to, cereals such as rice, barley, wheat, rye, oats, corn and sorghum; legumes such as soybeans, azuki beans, broad beans, green peas and peanuts; fruit trees and fruits such as apples, citrus fruits, pears, grapes, peaches, plums, cherries, walnuts, almonds, bananas and strawberries; vegetables such as cabbages, tomatoes, spinach, broccoli, lettuce, onions, welsh onions and green peppers; root vegetables such as carrots, potatoes, sweet potatoes, Japanese radishes, lotus roots and turnips; crops for processing such as cotton, hemp, paper mulberry, oriental paperbush, rapeseeds, beet, hops, sugarcane, sugar beet, olives, rubber, coffee, tobacco and tea; gourd such as Japanese pumpkins, cucumbers, watermelons and melons; pasture grass such as orchardgrass, sorghum, timothy, clover and alfalfa; lawn grass such as Korean lawn grass and bent grass; spice and aromatic crops such as lavender, rosemary, thyme, parsley, pepper and ginger; and herbs.

In the method of the present invention for using the plant growth regulator or for regulating plant growth, the above-described formulation containing flubendiamide may be used as it is or used after appropriately diluted or suspended in water etc. The desired plant growth regulating effect can be obtained by, for example, spray treatment (onto foliage etc.), coating treatment or injection treatment of target crops; spray treatment or drench treatment of the soil in the vicinity of target crops; or seed treatment (dust coating, dipping, etc.) of target crops with the use of an effective amount of the optionally diluted or suspended formulation. In the case of paddy-field rice, submerged treatment in paddy fields, nursery box treatment, etc. can also be performed with granules and the like. The time of treatment is, for example, sometime during the period from seed treatment to before seeding, or the time when crops have grown to some extent after seeding, and at any stage, the desired plant growth regulating effect can be obtained. However, the best time is selected depending on the kind of target crop and the intended plant growth regulating effect. To attain the goal of yield increase, the time of treatment is preferably at one month before harvest or earlier, and in the case of cereals such as rice and wheat, the time of treatment is preferably before heading.

The amount of the plant growth regulator used for treatment is appropriately adjusted depending on various factors, for example, the purpose, the kind of target crop, the crop growing conditions, the weather, the environmental conditions, the formulation, the application method, the application site, the application time, etc. For example, in the case where target crops are subjected to spray treatment, the amount of flubendiamide is in the range of about 20 to 500 g/ha; and in the case where the soil in the vicinity of target crops is subjected to drench treatment, the amount of flubendiamide is in the range of about 10 to 300 g/ha. When the amount used for treatment is within the above range, the plant growth regulating effect of the plant growth regulator of the present invention can be more preferably exerted.

In recent years, genetically modified crops (e.g., herbicide-tolerant crops, insect pest-resistant transgenic crops producing insecticidal proteins, disease-resistant transgenic crops producing inducers of disease resistance, palatability-enhanced crops, long-term preservable crops, high-yield crops, etc.) and IPM (integrated pest management) technology using insect sex pheromones (e.g., communication disrupting agents against Tortricidae and Hadeninae, etc.), natural enemy insects, etc. have made progress, and these technologies and the agrochemical composition of the present invention can be used in combination or used systematically.

The plant growth regulator of the present invention can be used simultaneously with agricultural and horticultural microbicides, agricultural and horticultural insecticides, agricultural and horticultural herbicides, synergists, phytotoxicity reducers, etc. for control of diseases/insect pests, weeds, etc. which may spread in the period for the application of the plant growth regulator, enhanced effects, reduced phytotoxicity to crops, and other purposes.

Non-limiting examples of typical compounds used as the agricultural and horticultural microbicides, the agricultural and horticultural insecticides, the agricultural and horticultural herbicides, the synergists and the phytotoxicity reducers are listed below.

Examples of the agricultural and horticultural microbicides include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isofetamid, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, chinomethionat, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, salicylanilide, zarilamid, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfuram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thioquinox, thiochlorfenphim, thiophanate, thiophanate-methyl, thicyofen, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, tolprocarb, natamycin, nabam, nitrostyrene, nitrothal-isopropyl, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, ferbam, famoxadone, fenapanil, fenamidone, fenaminosulf, fenarimol, fenitropan, fenoxanil, ferimzone, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, inorganic microbicides such as basic copper chloride, basic copper sulfate and silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, oxine copper, zinc sulfate and copper sulfate pentahydrate.

Examples of the agricultural and horticultural insecticides include 3,5-xylyl methylcarbamate (XMC), crystalline protein toxins produced by *Bacillus thuringiensis* such as *Bacillus thuringiensis* aizawai, *Bacillus thuringiensis* israelensis, *Bacillus thuringiensis* japonensis, *Bacillus thuringiensis* kurstaki and *Bacillus thuringiensis* tenebrionis, BPMC, Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, afidopyropen, avermectin-B, amidoflumet, amitraz, alanycarb, aldicarb, aldoxycarb, aldrin, alpha-endosulfan, alpha-cypermethrin, albendazole, allethrin, isazofos, isoamidofos, isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluoron, bisultap, hydramethylnon, hydroxy propyl starch, binapacryl, bifenazate, bifenthrin, pyflubumide, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, phenisobromolate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, butathiofos, buprofezin, furathiocarb, prallethrin, fluacrypyrim, fluazinam, fluazuron, fluensulfone, flucycloxuron, flucythrinate, fluvalinate, flupyradifurone, flupyrazofos, flufiprole, flufenerim, flufenoxuron, flufenzine, flufenprox, fluproxyfen, flubrocythrinate, flumethrin, flurimfen, prothiofos, protrifenbute, flonicamid, propaphos, propargite (BPPS), profenofos, profluthrin, propoxur (PHC), flometoquin, bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Examples of the agricultural and horticultural herbicides include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA (4-chlorophenoxyacetic acid), 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, iofensulfuron, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, clacyfos, cliodinate, glyphosate, glufosinate, glufosinate-P, credazine, clethodim, cloxyfonac, clodinafop, clodinafop-propargyl, clopyralid, cloproxydim, cloprop, clofop, clomazone, chlomethoxynil, chlomethoxyfen, clomeprop, chlorazifop, chlorazine, chloranocryl, chloramben, cloransulam, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlorbromuron, chlormequat, chloreturon, chloroxynil, chloroxuron, chlorotoluron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimidazon, dimexano, dimethachlor, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluoron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluoron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, triafamone, tri-allate, trietazine, tricamba, triclopyr, tridiphane, tritac, tritosulfuron, triflusulfuron, triflusulfuron-methyl, trifluralin, trifloxysulfuron, tripropindan, tribenuron, tribenuron-methyl, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluoron, haloxydine, haloxyfop, haloxyfop-P, haloxyfop-methyl, halosafen, halosulfuron, halosulfuron-methyl, bilanafos, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, butroxydim, flazasulfuron, flamprop, furyloxyfen, prynachlor, primisulfuron-methyl, fluazifop, fluazifop-P, fluazifop-butyl, fluazolate, fluoroxypyr, fluothiuron, fluometuron, fluoroglycofen, fluorochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, flumetsulam, fluridone, flurtamone, fluoroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Examples of the synergists include piperonyl butoxide, sesamex, sulfoxide, N-(2-ethylhexyl)-8,9,10-trinorborn-5-ene-2,3-dicarboximide (MGK 264), N-declyimidazole, WARF-antiresistant, TBPT, TPP, IBP, PSCP, methyl iodide, t-phenylbutenone, diethyl maleate, DMC, FDMC, ETP and ETN.

Examples of the phytotoxicity reducers include benoxacor, cloquintocet-mexyl, cyometrinil, daimuron, dichlormid, cyprosulfamide, fenchlorazole-ethyl, fenclorim, flurazole, fluxofenim, furilazole, mefenpyr-diethyl, MG191, oxabetrinil, allidochlor, isoxadifen-ethyl, cyprosulfamide, fluxofenim and 1,8-naphthalic anhydride.

EXAMPLES

Hereinafter, representative Examples and Test Examples in connection with the present invention are shown, but the present invention is not limited thereto. In Examples, the "parts" means parts by mass.

| Formulation Example 1. Emulsifiable concentrate | |
| --- | --- |
| Flubendiamide | 10 parts |
| Xylene | 70 parts |
| N-methyl pyrrolidone | 10 parts |
| Mixture of polyoxyethylene nonylphenyl ether and calcium alkylbenzene sulfonate | 10 parts |

The above ingredients are mixed and dissolved uniformly to give an emulsifiable concentrate.

| Formulation Example 2. Dust | |
| --- | --- |
| Flubendiamide | 3 parts |
| Clay powder | 82 parts |
| Diatomite powder | 15 parts |

The above ingredients are uniformly mixed and then pulverized to give a dust.

| Formulation Example 3. Granule | |
| --- | --- |
| Flubendiamide | 5 parts |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granule.

| Formulation Example 4. Wettable powder | |
| --- | --- |
| Flubendiamide | 20 parts |
| Kaolin and synthetic high-dispersion silicic acid | 75 parts |
| Mixture of polyoxyethylene nonylphenyl ether and calcium alkylbenzene sulfonate | 5 parts |

The above ingredients are uniformly mixed and then pulverized to give a wettable powder.

| Formulation Example 5. Flowable | |
| --- | --- |
| Flubendiamide | 30 parts |
| Sorpol 3105 (manufactured by Toho Chemical Industry Co., Ltd. Japan) | 5 parts |
| Propylene glycol | 5 parts |
| Rhodopol 23 (manufactured by Rhone-Poulenc S.A.) | 2 parts |
| Water | 58 parts |

The above ingredients are uniformly mixed and then dispersed in water to give a flowable.

Test Example 1

Effect on Increase in Stem Number (Promotion of Tillering) of Paddy Rice Plants

Paddy rice plants were transplanted to an experimental paddy field (50 m$^2$, planted with 1250 paddy rice plants on average), and 10 days later, granules containing flubendiamide as an active ingredient were applied once at the predetermined doses. At 43 days after the transplantation, in 10 rice plants chosen at random, the percentage of *Scirpophaga incertulas*-caused dead hearts per plant, the percentage of control of *Scirpophaga incertulas*, the stem number per plant, and the percentage of increase in the stem number were measured. To exclude the positive effect of the insecticidal action of flubendiamide on the growth of paddy rice plants, chlorantraniliprole, which has an equivalent insecticidal action, was used as a control agrochemical. The results are shown in Table 1.

TABLE 1

| Test agrochemical | Dose (g a.i./ha) | Percentage of S. incertulas-caused dead hearts (%) | Percentage of control of S. incertulas (%) | Stem number/plant | Percentage of increase in stem number (%) |
|---|---|---|---|---|---|
| Flubendiamide | 70 | 0.48 | 87.3 | 39.6 | 178 |
|  | 90 | 0.34 | 91.0 | 38.0 | 171 |
|  | 120 | 0.30 | 92.1 | 39.15 | 176 |
| Chlorantraniliprole | 40 | 0.37 | 90.2 | 26.35 | 119 |
| Non-treatment | — | 3.78 | 0.0 | 22.2 | 100 |

* The a.i. in the table stands for active ingredient.

As shown in Table 1, flubendiamide treatment and chlorantraniliprole treatment produced comparable results in terms of the percentage of Scirpophaga incertulas-caused dead hearts per plant and the percentage of control of Scirpophaga incertulas. If flubendiamide had not had plant growth regulating effect, both treatments would not have differed so much from each other in the increase in stem number per plant from the non-treatment level. In the chlorantraniliprole treatment plot, the stem number per plant was increased by about four compared with the non-treatment level, and the percentage of increase was about 120%. Meanwhile, in the flubendiamide treatment plots, regardless of dose, the stem numbers per plant were increased by about 17 compared with the non-treatment level, and the percentages of increase were about 170 to 180%. Thus, flubendiamide clearly showed a significant effect on the increase in stem number. These results suggest that chlorantraniliprole induced the increase in the stem number by controlling Scirpophaga incertulas, which may damage the stems of rice plants, while flubendiamide exerted plant growth regulating effect in addition to control effect on Scirpophaga incertulas, thereby promoted tillering of paddy rice plants and induced the increase in the stem number. The increase in the stem number induced by flubendiamide leads to the increase in harvest, namely, rice yield.

Test Example 2

Effect on Rooting Promotion and Plant Height Growth in Paddy Rice Plants

A 0.7% agar solution containing 25 ppm of flubendiamide was poured into a glass cylinder (3 cm diameter×10 cm) and allowed to be solidified. Onto the solidified agar, ten germinating rice seeds (variety: Nihonbare) were sown. Then, the top of the cylinder was covered with Japanese paper and the cylinder was placed in a thermostatic chamber (light-dark cycle: 16 hours of light and 8 hours of dark, relative humidity: 60 to 70%) at 25° C. At 8 days after the seeding, the lengths of the longest root (primary root) and the stem-and-leaf part extending from each seed-rice were measured and the averages were calculated. The percentages of elongation were also calculated with the proviso that the non-treatment levels were set as 100. The results are shown in Table 2.

TABLE 2

| Test agrochemical | Dose (ppm) | Average root length (cm) | Percentage of elongation in root length (%) | Average stem-and-leaf length (cm) | Percentage of elongation in stem-and-leaf length (%) |
|---|---|---|---|---|---|
| Flubendiamide | 25 | 6.7 | 160 | 3.9 | 170 |
| Non-treatment | — | 4.2 | 100 | 2.3 | 100 |

Since Test Example 2 was a laboratory test, there was no influence of insect pests and therefore the pure plant growth regulating effect of flubendiamide was shown. As shown in the results in Table 2, the effect of flubendiamide on root and stem-and-leaf elongation was observed, and the percentages of elongation in root and stem-and-leaf lengths were 160% and 170% of the non-treatment levels, respectively. Therefore, flubendiamide has an excellent plant growth regulating effect.

Test Example 3

Effect on Yield Increase (Increase in Numbers of Panicles and Unhulled Rice Grains) of Paddy Rice Plants Rice plants (variety: Takanari) of the 6.5- to 7-leaf stage were transplanted to 1-m$^2$ plots of a paddy field, and 2 or 12 days later, flubendiamide granules were applied at the predetermined doses. The test was performed in 4 replications. At 100 days after the transplantation, the rice plants were harvested, the numbers of panicles and unhulled rice grains per plant were measured and the averages were calculated. The percentages of increase were also calculated with the proviso that the non-treatment levels were set as 100. The results are shown in Table 3.

TABLE 3

| Test agrochemical | Dose (g a.i./ha) | Days after transplantation | Panicle number/plant | Percentage of increase (%) | Unhulled rice grain number/plant | Percentage of increase (%) |
|---|---|---|---|---|---|---|
| Flubendiamide | 70 | 2 | 11.2 | 119 | 1484.0 | 120 |
|  |  | 12 | 12.5 | 132 | 1600.0 | 130 |
|  | 35 | 2 | 10.4 | 110 | 1360.3 | 110 |
|  |  | 12 | 11.9 | 126 | 1528.0 | 124 |
| Non-treatment |  |  | 9.5 | — | 1234.2 | — |

As shown in the results of Test Example 3, in the flubendiamide treatment plots, regardless of application time and dose, the numbers of panicles and unhulled rice grains were significantly increased from the non-treatment levels. Therefore, flubendiamide has an excellent effect on yield increase.

The invention claimed is:

1. A method for increasing the yield of paddy rice, comprising treatment of the paddy rice or soil in the vicinity of the paddy rice with a plant growth regulator consisting essentially of flubendiamide as an active ingredient.

2. A method for promoting the growth of paddy rice, comprising treatment of the paddy rice or soil in the vicinity of the paddy rice with a plant growth regulator consisting essentially of flubendiamide as an active ingredient.

* * * * *